United States Patent
Baccelli et al.

(10) Patent No.: US 9,492,207 B2
(45) Date of Patent: Nov. 15, 2016

(54) VERTEBRAL ATTACHMENT DEVICE

(75) Inventors: Christian Baccelli, Saucats (FR); Regis Le Couedic, Bordeaux (FR)

(73) Assignee: Implanet, Societe Anonyme, Martillac (FR)

( * ) Notice: Subject to any disclaimer, the term of this patent is extended or adjusted under 35 U.S.C. 154(b) by 0 days.

(21) Appl. No.: 13/541,271

(22) Filed: Jul. 3, 2012

(65) Prior Publication Data

US 2012/0271354 A1 Oct. 25, 2012

Related U.S. Application Data

(63) Continuation of application No. PCT/FR2011/000005, filed on Jan. 5, 2011.

(30) Foreign Application Priority Data

Jan. 6, 2010 (FR) .................................... 10 00040

(51) Int. Cl.
*A61B 17/70* (2006.01)

(52) U.S. Cl.
CPC ........ *A61B 17/7053* (2013.01); *A61B 17/7032* (2013.01); *A61B 17/7041* (2013.01)

(58) Field of Classification Search
CPC .......... A61B 17/7022; A61B 17/7053; A61B 17/6466; A61B 17/6458
USPC ......... 606/74, 246, 263, 277, 278, 324, 330, 606/247–253, 276, 305, 319, 54–59
See application file for complete search history.

(56) References Cited

U.S. PATENT DOCUMENTS

| 4,887,596 A | 12/1989 | Sherman |
| 4,920,959 A * | 5/1990 | Witzel ................. A61B 17/645 606/53 |
| 4,950,269 A | 8/1990 | Gaines, Jr. |

(Continued)

FOREIGN PATENT DOCUMENTS

| EP | 1138268 A1 | 10/2001 |
| EP | 2047813 A1 | 4/2009 |

(Continued)

OTHER PUBLICATIONS

International Search Report issued in corresponding International Application No. PCT/FR2011/000005 dated Mar. 3, 2011.

*Primary Examiner* — Jan Christopher Merene
*Assistant Examiner* — Atiya Mahmud
(74) *Attorney, Agent, or Firm* — Banner & Witcoff, Ltd.

(57) ABSTRACT

A vertebral attachment system and method for retaining a spinal vertebra (25) on a rod (2) employ a device (1) including a body (3) for attachment to the rod, a flexible strip (4) for linking the vertebra to the attachment body and a means (5) for adjustably locking the flexible strip on the attachment body. The attachment body (3) is made of a single part having a U-shaped cross-section, for passing the rod between the bottom wall (10) of the U and the adjustable locking means. The adjustable locking means (5) consists of a linking part (18) connecting the opposite ends of the two arms (6, 7) of the U, arranged such as to compress the rod against the wall. The arms (6, 7) each include a recess (14) opposite thereof, located on the bottom side of the U, for passing the two ends of the strip between the bottom and the rod in order to form a loop for attachment to a vertebra.

15 Claims, 2 Drawing Sheets

(56) References Cited

U.S. PATENT DOCUMENTS

| | | | |
|---|---|---|---|
| 5,030,220 A | 7/1991 | Howland | |
| 5,129,388 A | 7/1992 | Vignaud et al. | |
| 5,176,680 A | 1/1993 | Vignaud et al. | |
| 5,335,400 A | 8/1994 | Sales | |
| 5,380,325 A | 1/1995 | Lahille et al. | |
| 5,383,905 A | 1/1995 | Golds et al. | |
| 5,534,002 A | 7/1996 | Brumfield et al. | |
| 5,662,653 A * | 9/1997 | Songer | A61B 17/7032 606/265 |
| 5,669,917 A | 9/1997 | Sauer et al. | |
| 5,676,665 A | 10/1997 | Bryan | |
| 5,746,741 A * | 5/1998 | Kraus et al. | 606/54 |
| 5,776,135 A * | 7/1998 | Errico et al. | 606/266 |
| 5,782,831 A | 7/1998 | Sherman et al. | |
| 5,810,817 A * | 9/1998 | Roussouly | A61B 17/7041 606/250 |
| 5,928,233 A | 7/1999 | Apfelbaum et al. | |
| 5,938,663 A | 8/1999 | Petreto | |
| 5,964,769 A | 10/1999 | Wagner et al. | |
| 5,976,133 A * | 11/1999 | Kraus | A61B 17/171 606/54 |
| 6,086,590 A * | 7/2000 | Margulies et al. | 606/263 |
| 6,179,838 B1 | 1/2001 | Fiz | |
| 6,248,104 B1 * | 6/2001 | Chopin | A61B 17/7041 606/267 |
| 6,248,106 B1 | 6/2001 | Ferree | |
| 6,290,700 B1 | 9/2001 | Schmotzer | |
| 6,296,643 B1 | 10/2001 | Hopf et al. | |
| 6,299,614 B1 | 10/2001 | Kretschmer et al. | |
| 6,309,390 B1 | 10/2001 | Le Couedic et al. | |
| 6,334,240 B1 | 1/2002 | Li | |
| 6,339,867 B1 | 1/2002 | Azam | |
| 6,402,751 B1 | 6/2002 | Hoeck et al. | |
| 6,514,255 B1 | 2/2003 | Ferree | |
| 6,554,831 B1 * | 4/2003 | Rivard et al. | 606/253 |
| 6,564,838 B1 | 5/2003 | Cruickshank | |
| 6,569,164 B1 | 5/2003 | Assaker et al. | |
| 6,613,049 B2 * | 9/2003 | Winquist | A61B 17/6458 606/54 |
| 6,652,526 B1 * | 11/2003 | Arafiles | 606/308 |
| 6,656,185 B2 | 12/2003 | Gleason et al. | |
| 6,673,073 B1 | 1/2004 | Schafer | |
| 6,749,361 B2 * | 6/2004 | Hermann et al. | 403/399 |
| 6,761,720 B1 | 7/2004 | Senegas | |
| 7,141,051 B2 * | 11/2006 | Janowski et al. | 606/272 |
| 7,481,828 B2 | 1/2009 | Mazda et al. | |
| 8,128,635 B2 | 3/2012 | Belliard et al. | |
| 8,172,843 B2 | 5/2012 | Baccelli et al. | |
| 2002/0007184 A1 * | 1/2002 | Ogilvie et al. | 606/61 |
| 2002/0120272 A1 | 8/2002 | Yuan et al. | |
| 2003/0153915 A1 | 8/2003 | Nekozuka et al. | |
| 2004/0097942 A1 | 5/2004 | Allen et al. | |
| 2005/0131404 A1 | 6/2005 | Mazda et al. | |
| 2008/0045955 A1 * | 2/2008 | Berrevoets et al. | 606/61 |
| 2008/0058818 A1 * | 3/2008 | Schwab | 606/73 |
| 2008/0208257 A1 * | 8/2008 | Matthys | 606/278 |
| 2008/0306551 A1 * | 12/2008 | Sanders et al. | 606/301 |
| 2009/0093843 A1 | 4/2009 | Lemoine et al. | |
| 2009/0182379 A1 | 7/2009 | Baccelli et al. | |
| 2009/0248077 A1 | 10/2009 | Johns | |
| 2009/0318969 A1 * | 12/2009 | Matthis et al. | 606/254 |
| 2009/0318973 A1 * | 12/2009 | Moulin et al. | 606/278 |
| 2010/0249845 A1 * | 9/2010 | Meunier et al. | 606/263 |
| 2012/0059377 A1 | 3/2012 | Belliard | |

FOREIGN PATENT DOCUMENTS

| | | |
|---|---|---|
| FR | 2694182 A1 | 2/1994 |
| FR | 2842724 A1 | 1/2004 |
| FR | 2890850 A1 | 3/2007 |
| WO | 94/26192 A1 | 11/1994 |
| WO | 02/09604 A1 | 2/2002 |
| WO | 2006/034423 A2 | 3/2006 |
| WO | 2009/013397 A1 | 1/2009 |
| WO | 2009/130276 A1 | 10/2009 |
| WO | 2009/141393 A1 | 11/2009 |

* cited by examiner

VERTEBRAL ATTACHMENT DEVICE

CROSS REFERENCE TO RELATED APPLICATION

This application is a continuation of co-pending International Application No. PCT/FR2011/000005, filed Jan. 5, 2011, the contents of which are hereby incorporated by reference in their entirety.

BACKGROUND OF THE INVENTION

The present invention relates to a vertebral fixing device for securing a rachidian vertebra to a rod, comprising a fixing body on the rod, a flexible strip for linking said vertebra with the fixing body and adjustable means for blocking the flexible strip on the fixing body.

It is particularly importantly applicable, although not exclusively applicable, in the field of the straightening of the spinal column of a patient having an abnormal curvature.

In this case, since the vertebrae are not correctly aligned relative to one another relative to the vertebral axis, they exhibit mutual inclinations.

In some places, the lateral edges of the vertebrae will therefore be, on one side, close to one another, and on the other side, distant from one another.

In order to straighten the assembly, it is known to reset to a substantially equivalent distance the lateral edges of the vertebrae on either side of the spinal column, by the use of rods linking together, either screws, that are inserted into the vertebrae themselves, or hooks, that are introduced along the rachidian channel.

Such devices do, however, present drawbacks.

The use of screws is first of all possible only if the vertebrae are in good condition and/or wide enough at the level of the fixing.

The use of hooks is very delicate since the operator must not touch the spinal cord for fear of paralyzing the patient.

To mitigate these drawbacks, there has been proposed (FR 02 09 317) a system that makes it possible to avoid the fixing screws or hooks.

The system comprises a flexible link for fixing the vertebra to a link part which is in turn fixed to the straightening rod.

Means for blocking the flexible link by reclosing the link part on the rod are provided. However, here again, this system does present drawbacks.

In practice it requires, on the one hand, an articulation of the link part so as to allow for the lateral insertion of the rod and of the flexible link, and, on the other hand, a fixing of the link to the part to allow for such blocking after the part has been reclosed on the rod.

Also known (EP 2 047 813) is a vertebral fixing device comprising a body for fixing a flexible strip on a rod, in the form of an articulated jaw.

Each branch of the jaw is provided with an orifice for the passage of one of the two strands of a loop of the strip, designed to be blocked at the bottom of said jaw by the rod once the jaw is reclosed and screwed.

The articulated device is fragile and does not allow for an easy adjustment of the flexible strip.

The same document describes another system, this time formed by a cylindrical part provided with a bottom orifice for the passage of the loop, and two top slots through which the free strands exit allowing the two strands to be wedged against the inner face of the cylinder by the use of a semi-cylindrical element, of a height substantially equal to the length of the part, and a screw for compressing said element onto the strands of the loop.

Such a system which clearly does not concern the securing of a vertebra on a cylindrical rod notably does not allow for easy placement, and notably requires a guiding tool.

Also known (WO 2009/013397) is a vertebral fixing device for a system for correcting abnormal curvatures of the vertebral column using a clamping collar consisting of a notched flexible strip passing into a part folded in two for fixing between its two branches a rod with opening for attaching the collar by notching. Such a device is difficult to adjust, and once tightened does not allow for the tightening to be repeated.

SUMMARY OF SELECTED INVENTIVE ASPECTS

The present invention aims to provide a vertebral fixing device that provides a better response than those previously known to the requirements of the practise, notably in that it will allow for a much wider flexibility, a better solidity by virtue of the absence of mechanical articulation which is always liable to blocking, and in that it offers much improved adjustment possibilities, and all for a lower cost.

To this end, the invention essentially proposes a vertebral fixing device for securing a rachidian vertebra to a cylindrical rod, comprising a fixing body on the rod, a flexible strip for linking said vertebra with the fixing body and adjustable means for blocking the flexible strip on the fixing body, the fixing body being of U-shaped cross section, for passage of the rod between the bottom wall of the U and the adjustable blocking means, said adjustable blocking means being formed by a link part linking the facing ends of the two branches of the U, said branches each comprising a facing void situated on a side of the bottom of the U, namely a first void for the passage of the free ends and a second void on the other side for the passage of the strip specifically for forming a fixing loop on the vertebra, characterized in that the body is formed of a single part, and in that the link part is formed by a clamping screw provided, on the one hand, with a head for passage into a first branch of the U, said head including a tapered part arranged to compress the rod as it is screwed, and thus compress the two ends of the flexible strip against the wall, and, on the other hand, an end for screwing onto the opposite branch of the U.

The expression "single-piece body" should be understood to mean a rigid single-piece part.

During the tightening for fixing, the fact that the loop has two initially non-compressed free strands, the rod being in position, namely two strands, one against the other, not compressed, facing the rod, allows for a relative slippage of the link relative to the fixing body, and because of this a highly flexible adjustment that does not generate shear stresses on the vertebra and/or on the fixing body. The latter can also remain positioned facing the surgeon and the screw tightening tool.

Such an adaptive slip possibility, not allowed by the prior art either because of the fixing of the link to the fixing body, or because of an articulation whose jaws, to be fixed to one another, necessarily cause an initial compression on the rod itself, emerged as a factor of inaccuracy and of poor retention of the link on the rod.

With the invention and notably by virtue of the wedging effect obtained by the link part, that is no longer the case.

In advantageous embodiments, there is also a recourse to one and/or other of the following arrangements:

the bottom wall of the U is of semi-cylindrical form, complementing the shape of the rod, terminated on either side by longitudinal flanges allowing the rod to be clipped in the bottom of the U by virtue of a deformation of the branches.

It is then possible for the surgeon to prefix the rod with the body accurately, while also allowing possibilities for longitudinal slipping of the body along the rod. The clipping is in fact light and serves only a holding function, without exerting pressure on the bar and on the facing strands in the bottom of the U;

the head of the clamping screw also includes a shoulder designed to cooperate with the outer face of the first branch of the U.

Such a shoulder, when it comes into abutment, thus indicates to the surgeon that he has obtained the appropriate tightening. It may also have a complementary tightening role.

Since the branches of the U are free, the part in fact has a certain flexibility during the tightening, the distance between the ends of the branches of the U then being slightly adjustable, with pinching effect;

the fixing body, the rod and the link part are made of titanium;

the fixing body is made of polymer material;

the bottom of the U includes complementary blocking notches that work by friction;

the notches are parallel to the longitudinal axis of the bottom of the U (or to the longitudinal plane of symmetry of the part), with flat top;

the notches are non-return notches, parallel in the longitudinal plane of the U, and having edges forming angles opposite or perpendicular to the direction of slip towards the tightening of the loop;

the flexible strip is a braid made of polymer.

The invention also relates to a system for straightening a spinal column comprising at least two devices as described above and at least one rod.

Advantageously it comprises two rods and at least four devices.

The invention also relates to a method for fixing a rachidian vertebra to a rod implementing a device and/or system as described above.

The invention also proposes a method for fixing a rachidian vertebra to a rod, in which a flexible strip is passed around a part of the vertebra to form a loop clamping said part whose free ends exit on the side retained for fixing to the rod, and said free ends are passed into two voids of a single-piece fixing body on the rod, of U-shaped cross section, each void being situated in a respective branch of the U and on the side of the bottom of the U, characterized in that the rod is introduced by clipping via the opening of the U, so that the free ends are seized between the rod and the bottom of the U, the tension of the loop on the vertebra part is adjusted by simultaneously pulling on the strands, and the rod is progressively compressed against the strands to block them in translation by adjustable blocking means, said adjustable blocking means being formed by a link part linking the facing ends of the two branches of the U.

Advantageously, the link part being formed by a clamping screw provided, on the one hand, with a head for passage into a first branch of the U, said head including a tapered part directed towards the other branch and, on the other hand, an end for screwing to the opposite branch of the U, said clamping screw is screwed so that the rod is compressed by the tapered part as it is screwed, and the two ends of the flexible strip are thus compressed against the wall of the bottom of the U.

Also advantageously, the screwing is stopped by blocking of a shoulder of the screw head on the outer face of the first branch of the U.

In an advantageous embodiment, at least two loops are formed by passing their respective ends into at least two fixing bodies as described above, then they are clipped and compressed by screwing on one and the same rod.

BRIEF DESCRIPTION OF THE DRAWINGS

The invention will be better understood from reading the following description of embodiments given hereinbelow as nonlimiting examples.

The description refers to the accompanying drawings in which.

DETAILED DESCRIPTION OF EXAMPLE EMBODIMENTS

Hereinafter in the description, the same reference numbers will be used to designate the same elements.

Figure 1:
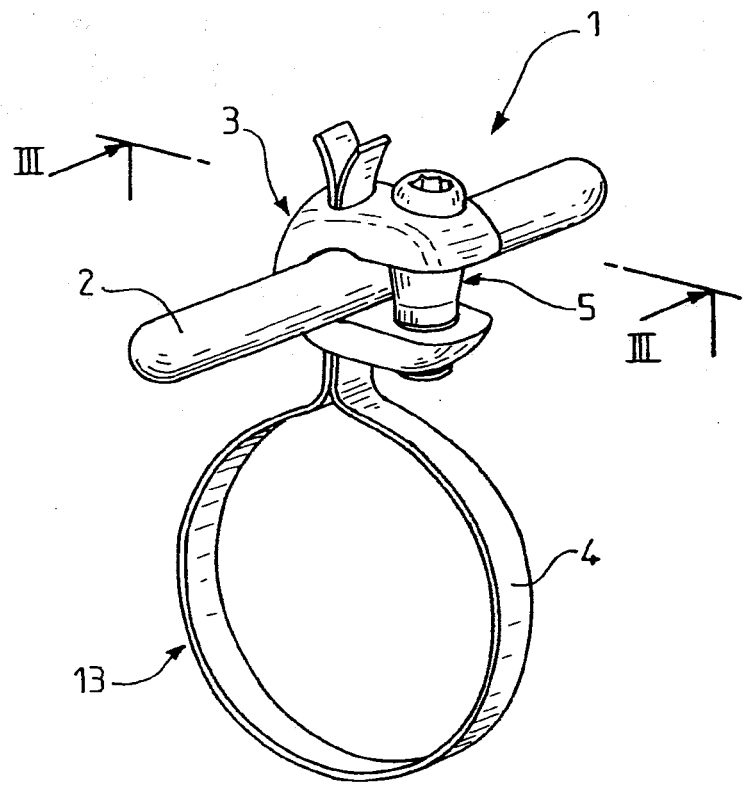
FIG. 1 is a perspective view of the device according to the invention.

FIG. 1 shows a vertebral fixing device 1 for securing a rachidian vertebra (not represented) to a cylindrical rod 2.

The device comprises a fixing body 3 on the rod and a flexible strip 4 made of braided polymer, for example of polyester, 6 mm wide and thirty centimeters long.

It also comprises adjustable means 5 for blocking the flexible strip on the fixing body 3.

Figure 2:
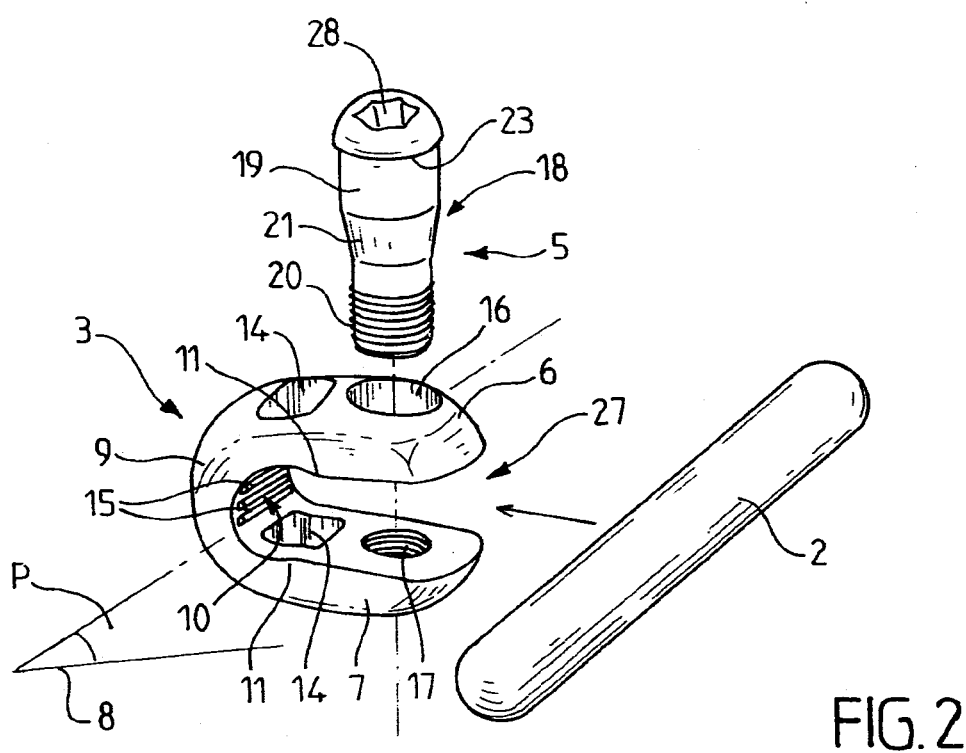
FIG. 2 shows an embodiment of the body, of the blocking means and of the joining rods separated from one another, according to the invention.

More specifically with reference to FIG. 2, the body 3 is formed by a single-piece part forming a clamp having a U-shaped cross section, said U comprising two thick branches 6 and 7 of substantially semi-oval-shaped cross section, symmetrical relative to a longitudinal plane 8, and linked together by a link part 9 in the form of a half torroidal ring forming, on one side, the semi-cylindrical bottom 10 of the U, and, on the other side, a rounded outer wall of the torroidal surface.

The bottom wall of the U is of a shape complementing that of the rod 2 or substantially complementing same, and comprises longitudinal lips or flanges 11 allowing the rod to be clipped into the bottom of the U once the braid 4 is passed in double thickness to form the loop 13 (see FIG. 1).

Each branch 6, 7 includes a void 14, for example in the form of a wide slot, for example 5 to 10 times wider than the thickness of the braid to facilitate its introduction during the operation.

The bottom 10 of the U also includes non-return blocking notches 15, parallel to the longitudinal plane 8 and having, in a manner known per se, edges forming angles opposite or perpendicular to the direction of slip, opposing the untightening of the loop once the tightening is done.

Each branch 6 and 7 includes a cylindrical orifice respectively 16 and 17 for passage of the blocking means 5, namely a bore 16 of the diameter D and a tapped cylindrical orifice 17 for screwing of diameter d<D.

The blocking means 5 are formed by a link part 18, or screw, provided on one side with a head 19 for passage into the bore 16 of the U, and on the other side an end 20 for screwing into the tapped orifice 17.

The head 19 of the part 18 comprises a top cylindrical part which cooperates with soft friction with the bore 16, said top part being securely connected with a tapered bottom part 21, narrowing towards the bottom and arranged to compress (bearing 22 in FIG. 3) the rod 2 as the part is screwed.

In the embodiment that is more particularly described here, the head of the screw also includes a shoulder 23, for example tapered, designed to cooperate with the outer face 24 of the first branch of the U and to serve as an abutment to stop the screwing.

Figure 3:
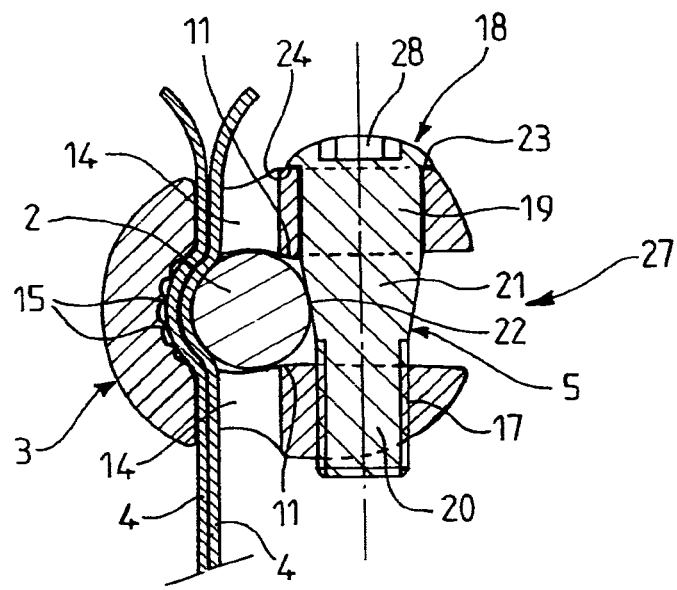
FIG. 3 is a cross-sectional view through III III of the device of FIG. 1.
Figure 4:
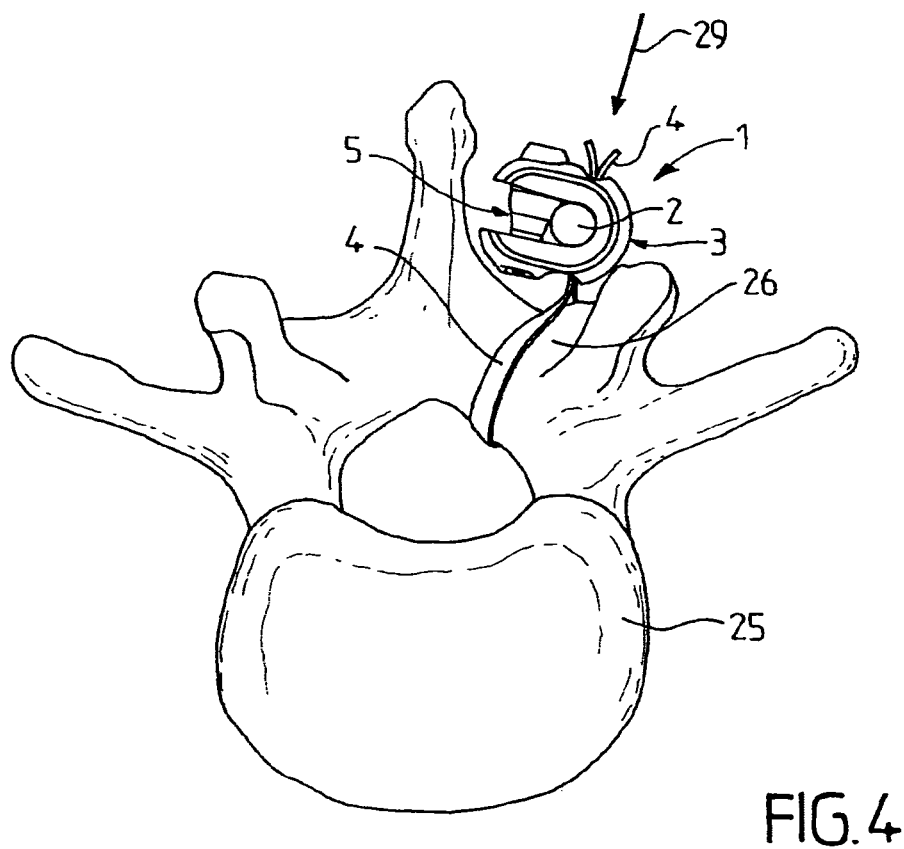
FIG. 4 is a plan view showing the device of FIG. 1 fixed to a vertebra.

There now follows a description with reference to FIGS. 2, 3 and 4 of the fitting of the device 1 on the vertebra 25 (see FIG. 4).

The device 1 described above makes it possible to mechanically connect the flexible braid 4 to the rod providing the metal join 2 with the vertebra 25.

This implant is particularly indicated in the context of scoliosis-type vertebral column surgery.

The braid 4 is introduced beforehand into the body 3 while enclosing a part 26 of the rachidian anatomy (in this case, the transverse blade, posterior arc) in a loop.

The same operation is performed on the vertebra or vertebrae on the side on which they are to be repositioned relative to one another, in this case to repair the scoliosis.

Once the loops are made, the joining rod 2 is introduced by clipping by the side via the openings 27 of the Us of the bodies 3.

Hereinafter, there follows only a description of the fixing of a single body, the fixings of the others being performed in the same way once their respective positions are fixed along the rod.

The screw 18 is inserted into the bore 16 then begins to be screwed into the bore 17.

The screwing is done by the surgeon who has access to the screw heads each provided with a screwing orifice and/or void 28 that is known per se (see arrow 29 in FIG. 4).

Once everything is prepositioned and when there is still play on the braids, the latter are pulled so as to tighten the loops onto the blades of the respective vertebrae.

The non-return edges 15 allow for tightening in one direction and prevent untightening in the other when the two ends of the flexible strip still have a little mobility.

Then the screwing of the screws 19 enables the tapered parts 21 to gradually bear on the joining rod 2 until the assembly is locked by blocking for each device by tightening the braid 4 between the bottom of the U and the joining rod.

As is clearly evident and as also results from the foregoing, the present invention is not limited to the embodiments that are more particularly described. On the contrary, it encompasses all the variants and notably those in which two or more rods are fixed in succession or on either side of the vertebral column. It is to be noted that herein the terms "compress" and "press" are used interchangeably and in various forms and, in accordance with the original disclosure of parent application PCT/FR2011/000005, neither term is intended to imply a reduction of size or volume, or a deformation, as a requirement.

The invention claimed is:

1. A vertebral fixing device for securing a rachidian vertebra to a cylindrical rod, comprising a fixing body on the rod, a flexible strip for linking said vertebra with the fixing body and adjustable means for blocking the flexible strip on the fixing body, the fixing body being of U-shaped cross section, for passage of the rod between a bottom wall of the U and the adjustable blocking means, said adjustable blocking means being formed by a link part linking facing ends of two branches of the U, said branches each comprising a facing void situated on a side of the bottom wall of the U, having a bottom above the bottom wall of the U, namely a first void with a bottom above the bottom wall of the U for passage of free ends of the flexible strip and a second void having a bottom above the bottom wall of the U on the other side for passage of the strip specifically for forming a fixing loop on the vertebra, wherein:

the body is formed of a rigid single part;

the link part is formed by a clamping screw provided with a head for passage into a first branch of the U, said head including a tapered part arranged to engage and progressively compress the rod against the bottom wall of the U as it is screwed such that the rod is positioned at least partially below said respective bottoms of said first and second voids, and thus progressively compress any two flexible strip portions passing between said first and second voids against the bottom wall of the U an amount corresponding to an advancement amount of the clamping screw, said clamping screw further having an end for screwing onto a second branch of the U opposite the first; and the head of the clamping screw also includes a shoulder designed to abut with an outer face of the first branch of the U, said shoulder being configured in relation to the tapered part such that as the screw is advanced, and with said flexible strip portions positioned between the rod and the bottom wall of the U, said tapered part engages the rod to progressively press the flexible strip portions between the rod and the bottom of the U, substantially only up to a point that the shoulder abuts with the face of the first branch of the U, and without substantial deflection of either of the two branches of the U.

2. The device according to claim 1, wherein the bottom of the U includes complementary blocking notches that work by friction.

3. The device according to claim 2, wherein the notches are parallel to the longitudinal axis of the bottom of the U, with flat top.

4. The device according to claim 3, wherein the notches are non-return notches, parallel to the longitudinal axis of the bottom of the U, and having edges forming angles opposite or perpendicular to a direction of slip towards the tightening of the loop.

5. A system for straightening a spinal column on a rod comprising at least two devices according to claim 1, said system comprising said cylindrical rod on which are fixed said devices.

6. The system according to claim 5, said system comprising two rods and at least four devices.

7. The device according to claim 1, wherein the fixing body, the rod and the link part are made of titanium.

8. The device according to claim 1, characterized in that the flexible strip is a braid made of polymer.

9. The device according to claim 1, wherein said link part extends substantially perpendicularly to the two branches of the U.

10. The device according to claim 1, wherein said head forms a proximal end of said clamping screw and said tapered part is arranged distal of said proximal end, and proximal of said end for screwing onto the second branch of the U.

11. A vertebral fixing device comprising a fixing body, a flexible strip and an adjustable member for blocking a flexible strip on the fixing body, the fixing body having a U-shape, allowing for passage of a rod between a bottom wall of the U and the adjustable blocking member, said adjustable blocking member being formed by a link part linking the ends of first and second branches of the U, said branches each comprising a void having a bottom above the bottom wall of the U, namely a first void with a bottom above the bottom of the U for the passage of free ends of the flexible strip and a second void having a bottom above the bottom of the U on the other side for passage of the strip for forming a fixing loop, wherein:

the body is a rigid body;

the link part is provided with a head for passage into a first branch of the U, said head forming a proximal end of said link part and including a pressing part arranged distal of said proximal end to press against a said rod passed through said fixing device and progressively compress the rod against the bottom of the U such that the rod is positioned at least partially below said respective bottoms of said first and second voids, as the link part is advanced, and thus also compress any two portions of the flexible strip present between the rod and wall and passing between said first and second voids an amount corresponding to an advancement amount of the link part, said link part further having a distal end, distal of said pressing part, for advanceably engaging the opposite second branch of the U; and the head of the link part includes a shoulder designed to abut with an outer face of the first branch of the U, said shoulder being configured in relation to the pressing part such that as the link part is advanced, and with said flexible strip portions positioned between the rod and the bottom wall of the U, said pressing part engages the rod to progressively press the flexible strip portions between the rod and the bottom of the U, substantially only up to a point that the shoulder abuts with the face of the first branch of the U, and without substantial deflection of either of the two branches of the U.

12. The device according to claim 11, wherein the link part comprises, at its distal end, a screw threadably engageable with the second branch of the U.

13. The device according to claim 11, wherein said body is formed of a single part.

14. The device according to claim 11, wherein the pressing part is a tapered part.

15. The device according to claim 11, wherein said link part extends substantially perpendicularly to the two branches of the U.

* * * * *